(12) United States Patent
Korol et al.

(10) Patent No.: US 6,806,399 B1
(45) Date of Patent: Oct. 19, 2004

(54) POLLEN-MEDIATED METHOD FOR TRANSFORMATION OF MAIZE, TOMATO OR MELON

(75) Inventors: Abraham Korol, Haifa (IL); Tzion Fahima, Haifa (IL); Eviator Nevo, Haifa (IL)

(73) Assignee: Carmel-Haifa University Economic Corporation Ltd., Haifa (IL)

(*) Notice: Subject to any disclaimer, the term of this patent is extended or adjusted under 35 U.S.C. 154(b) by 0 days.

(21) Appl. No.: 09/552,147

(22) Filed: Apr. 19, 2000

(51) Int. Cl.[7] ............................................. C12N 15/82
(52) U.S. Cl. ........................ 800/278; 800/282; 800/288
(58) Field of Search ................................ 800/278, 282, 800/288, 309, 300.1, 298, 320.1, 300, 317.4; 435/470, 419, 418

(56) References Cited

U.S. PATENT DOCUMENTS

| | | | |
|---|---|---|---|
| 5,122,466 A | 6/1992 | Stomp | 435/172.3 |
| 5,629,183 A | 5/1997 | Sanders | 435/172.3 |
| 5,929,300 A | * 7/1999 | Burke et al. | 800/278 |
| 6,002,068 A | 12/1999 | Lagrimini et al. | |

FOREIGN PATENT DOCUMENTS

| | | |
|---|---|---|
| EP | 0270256 A2 | 6/1988 |
| EP | WO 98/42870 | 1/1998 |
| RU | 1708849 | 1/1992 |
| WO | WO 94/28148 A1 | 12/1994 |
| WO | WO99/38979 A1 | 8/1999 |

OTHER PUBLICATIONS

Frame, B. R. et al., "Production of fertile transgenic maize plants by silicon carbide whisker–mediated transformation." 1994, The Plant Journal, vol. 6, pp. 941–948.*

Dupuis, I. and Pace, G. M. "Gene transfer to maize male reproductive structure by particle bombardment of tassel primordia." 1993, Plant Cell Reports, vol. 12, 607–611.*

Kaeppler, H. F. et al., "Silicon carbide fiber–mediated stable transformation of plant cells." 1992, Theor. Appl. Genet., vol. 84, pp. 560–566.* van der Leede–Plegt, L. M. et al., "Development of a pollen–mediated transformation method for *Nicotiana glutinosa*." Transgenic Research, vol. 4, pp. 77–86.*

Thompson et al Euphytica 1995, 85: 1–3.

Nester, EW., et al. (1984). Am. Rev. Plant Physio 35:387–413.

Lorz H., Baker B., Schel. J. (1985). Mol Gen Genet 199:178:182.

Fromm M.E., Taylor L.P., Walbot V. (1986). Nature 312:791–793.

Klein T.M., Kornstein L., Sanford J.C., Fromm M.E. (1987)., Nature 327:70–73).

Schell, J., Science 237:1176–1183 (1987).

Luo Z.X. and Wu R., 1988, Proc. Nat'l Acad. Sci USA 83:715–719.

* cited by examiner

*Primary Examiner*—Anne Kubelik
(74) *Attorney, Agent, or Firm*—Browdy and Neimark, P.L.L.C.

(57) ABSTRACT

A genotype-independent method for efficiently carrying out pollen-mediated transformation of maize, tomato or melon is described. The method uses pollen pretreated with silicon carbide and DNA to produce transformed plants with high efficiency and reproducibility.

26 Claims, 5 Drawing Sheets

POLLEN-MEDIATED METHOD FOR TRANSFORMATION OF MAIZE, TOMATO OR MELON

1. BACKGROUND OF THE INVENTION

The present invention relates to methods for plant genetic transformation and for products thereof. More specifically, the present invention relates to the genetic transformation of any plant species with sexual reproduction based on a pollination-fecundation process. According to the present invention, pollen grains are pre-treated with silicon carbide fibers and the transforming DNA. The present invention also involves pollinating recipient plants with pollen grains carrying the transforming DNA.

Advances in molecular biology have dramatically expanded man's ability to manipulate the germplasm of animals and plants. Genes controlling specific phenotypes, for example specific polypeptides that lend antibiotic or herbicide resistance, have been located within certain germplasm and isolated from it. Even more important has been the ability to take the genes which have been isolated from one organism and to introduce them into another organism. This transformation may be accomplished even where the recipient organism is from a different phylum, genus or species from that which donated the gene (heterologous transformation).

Genetic engineering of plants, which entails the isolation and manipulation of genetic material (usually in the form of DNA or RNA) and the subsequent introduction of that genetic material into a plant or plant cells, offers considerable promise to modern agriculture and plant breeding. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques. Once a gene has been identified, cloned, and engineered, it is still necessary to introduce it into a plant of interest in such a manner that the resulting plant is both fertile and capable of passing the gene on to its progeny.

Developments in agrobiotechnology have resulted in a tremendous expansion of the capabilities for the genetic engineering of plants. Many transgenic dicotyledonous plant species have been obtained. However, many species of plants, especially those belonging to the Monocotyledonae and particularly the Gramineae, including economically important species such as corn, wheat and rice, have proved to be very recalcitrant to stable genetic transformation. Difficulties have been encountered in achieving both: a) integrative transformation of monocot plant cells with DNA (i.e., the stable insertion of DNA into the nuclear genome of the monocot plant cells) and b) regeneration from transformed cells of phenotypically normal monocot plants, such as phenotypically normal, fertile adult monocot plants. It has been suggested that such difficulties have been predominantly due to the nonavailability of monocot cells that are competent with respect to: 1) DNA uptake, 2) integrative transformation with the taken-up DNA, and 3) regeneration of phenotypically normal, monocot plants from the transformed cells (Potrykus (1990) Bio/Technology 9:535).

Thus, the introduction of exogenous DNA into monocotyledonous species and subsequent regeneration of transformed plants has proven much more difficult than transformation and regeneration in dicotyledonous plants. Moreover, reports of methods for the transformation of monocotyledons such as maize, and subsequent production of fertile maize plants, have not been forthcoming. Consequently, success has not been achieved in this area and commercial implementation of transformation by production of fertile transgenic plants has not been achieved. Thus there is a particularly great need for methods for improving genetic characteristics. Problems in the development of genetically transformed monocotyledonous species have arisen in many general areas. For example, there is generally a lack of methods, which allow one to introduce nucleic acids into cells and yet permit efficient cell culture and eventual regeneration of fertile plants.

Genetic engineering techniques have been successfully applied principally in dicotyledonous species. The uptake of new DNA by recipient plant cells has been accomplished by various means, including Agrobacterium infection (Nester, E. W., et al, (1984). Am. Rev. Plant Physiol 35: 387–413), polyethylene glycol (PEG) mediated DNA uptake (Lorz H., Baker B., Schell J. (1985). Mol Gen Genet 199:178–182.), electroporation of protoplasts (Fromm M. E., Taylor L. P., Walbot V. (1986). Nature 312:791–793.) and microprojectile bombardment (Klein T. M., Kornstein L., Sanford J. C., Fromm M. E. (1987). Nature 327: 70–73.).

The Agrobacterium transformation system is among the recombinant DNA technologies for genetic manipulation of plant genotypes. Virulent strains of the soil bacterium *Agrobacterium turnefaciens* are known to infect dicotyledonous plants and to elicit a neoplastic response in these plants. The tumor-inducing agent in the bacterium is a plasmid that functions by transferring some of its DNA into its host plant's cells where it is integrated into the chromosomes of the host plant's cells. This plasmid is called the Ti plasmid, and the virulence of the various strains of *A. tumefaciens* is determined in part by the vir region of the Ti plasmid which is responsible for mobilization and transfer of the T-DNA (Schell, J., Science, 237: 1176–1183 (1987)). The T-DNA section is delimited by two 23-base-pair repeats designated right border and left border, respectively. Any genetic information placed between these two border sequences may be mobilized and delivered to a susceptible host. Once incorporated into a chromosome, the T-DNA genes behave like normal dominant plant genes. They are stably maintained, expressed and sexually transmitted by transformed plants, and they are inherited in normal Mendelian fashion.

There are two common ways to transform plant cells with Agrobacterium: cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Agrobacterium-mediated transformation in dicotyledons facilitates the delivery of larger pieces of heterologous nucleic acid as compared with other transformation methods such as particle bombardment, electroporation, polyethylene glycol-mediated transformation methods, and the like. In addition, Agrobacterium-mediated transformation appears to result in relatively few gene rearrangements and more typically results in the integration of low numbers of gene copies into the plant chromosome.

However, the Agrobacterium transformation system, as stated, is restricted to certain dicot crops. For the majority of monocots, especially cereals (graminae) and grasses, A tumefaciens mediated gene transfer is not possible. Thus, the most important cultivated plants are not accessible for effective gene transfer.

A second frequently used process for transformation of plants is DNA direct delivery. One form of direct DNA delivery is direct gene transfer into protoplasts (using polyethyleneglycol treatment and/or electroporation). Protoplasts for use in such direct gene transfer methods have most often been obtained from embryogenic cell suspension cultures (Lazzeri and Lorz (1988) Advances in Cell Culture, Vol. 6, Academic press, p. 291; OziasAkins and Lorz (1984) Trends in Biotechnology 2: 1 19). However, the success of such methods has been limited due to the fact that regeneration of phenotypically normal plants from protoplasts has been difficult to achieve for most genotypes. For example, while regeneration of fertile corn plants from protoplasts has been reported, these reported methods have been limited to the use of non-transformed protoplasts. Moreover, regeneration of plants from protoplasts is a technique, which carries its own set of significant drawbacks. Even with vigorous attempts to achieve fertile, transformed maize plants, reports of success in this regard have not been forthcoming.

In yet another form of direct transformation, the genetic material is transferred using high velocity ballistic penetration by small particles with the nucleic acid either within the matrix of small beads or particles, or on the surface (Klein, et al., Nature, 327:70–73 (1987)). In this method, non-biological particles may be coated with nucleic acids and delivered into cells by a propelling force. Exemplary particles include those comprised of tungsten, gold, platinum, and the like. The main advantage of particle bombardment over Agrobacterium is absence of biological incompatibilities found when using this biological vector. In the plant kingdom, particle bombardment has shown good utility for transformation of conifers, dicots and monocots. However, particle bombardment has certain drawbacks relating to cost, ease of use, accessibility and end product utility. Moreover, transgenic plants obtained via Agrobacterium generally contain more predictable introduced DNA's while partical bombardment, as well as other direct DNA uptake methods, give rise to more random and uncontrolled DNA integration events. Particle bombardment also often results in complex transgene insertion loci, which may cause gene silencing in some instances. In addition to their restrictive application in dicoytyledoneae and relatively low transformation rates, these systems require the regeneration of entire plants from plant protoplasts.

Thus, great difficulties remain also in employing methods of direct DNA delivery, due to high dependence on regeneration ability of the genotype. As a consequence, in the few known examples of successful transformation of maize the experimental material was based on the line A188 which is easy in regeneration. Noteworthy, in all of the methods based on multicellular target (embryos, leaf-discs or calli) the resulting transformed tissue is mosaic, demanding further steps to obtain non-mosaic progeny. Most of these difficulties are due to the use of long-term tissue culturing.

Another major problem in achieving successful monocot transformation has resulted from the lack of efficient marker gene systems, which have been employed to identify stably transformed cells. Marker gene systems are those, which allow the selection of, and/or screening for, expression products of DNA. For use as assays for transformed cells, the selectable or screenable products should be those from genetic constructs introduced into the recipient cells. Hence, such marker genes can be used to identify stable transformants.

Of the more commonly used marker gene systems are gene systems which confer resistance to aminoglycosides such as kanamycin. While kanamycin resistance has been used successfully in both rice (Yang et al., 1988) and corn protoplast systems (Rodes et al., 1988), it remains a very difficult selective agent to use in monocots due to high endogenous resistance (Hauptmann, et al., 1988). Many monocot species, maize, in particular, possess high endogenous levels of resistance to aminoglycosides. Consequently, this class of compounds cannot be used reproducibly to distinguish transformed from non-transformed tissue. New methods for reproducible selection of or screening for transformed plant cells are therefore needed. Accordingly, it is clear that improved methods and/or approaches to the genetic transformation of monocotyledonous species would represent a great advance in the art. Furthermore, it would be of particular significance to provide novel approaches to monocot transformation, such as transformation of maize cells, which would allow for the production of stably transformed, fertile corn plants and progeny into which desired exogenous genes have been introduced. The identification of marker gene systems applicable to monocot systems such as maize would provide a useful means for applying such techniques generally. The development of these and other techniques for the preparation of stable genetically transformed monocots such as maize could potentially revolutionize approaches to monocot breeding.

In order to overcome the difficulties of genotype-dependant transformation caused by low regeneration potential of cereals, many efforts were put to develop an alternative, genotype-independent transformation approach based on the pollination pathway (Ohta Y., 1986). In maize, high efficiency genetic transformation can be achieved by a mixture of pollen and exogenous DNA. (Luo Z. X. and Wu R., 1988, Proc. Natl. Acad. Sci. USA 83:715–719). Maize, often referred to as corn in the United Stated, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears. Transformation of rice via the pollen-tube pathway has also been demonstrated (Plant Molecular Biology Reporter 6:165–174). The major potential advantages of the pollen-tube pathway approach include: (a) genotype independence; (b) lack of mosaicism; (c) no need for complicated cell and tissue culture techniques.

Despite the keen interest in an effective transformation method having such advantages, no serious results have been obtained with this approach, because of low reproducibility. Nevertheless, partial transfer of alien genes into intact plants via pollination pathway has been reported in maize, tomato and melon (Chesnokov, Yu. V., et al, 1992, USSR Patent No. 1708849; Bulletin of the USSR Patents, No. 4; Chesnokov Yu. V. & Korol A. B. 1993; Genetika USSR, 29:1345–1355).

The procedures of genetic transformation based on the pollination-fecundation pathway include: (i) employment of a mixture (paste) of the pollen and transforming DNA; (ii) delivery of the alien DNA into the pollen tube, after pollination; and (iii) microparticle bombardment of microspores or pollen grains. The obstacles in application of the so-far developed versions of the pollination pathway of genetic transformation include: (i) very low reproducibility; (ii) extremely poor applicability to maize due to the very long style of this plant; and (iii) high cost (Potrykus, I. 1990.

Gene transfer to cereals: an assessment. Bio/Technology 8:535–542). The present invention provides an alternative highly efficient method of plant genetic transformation and in particular of maize genetic transformation employing pollen treatment with silicon carbide fibers in the presence of foreign DNA.

Silicon carbide fiber technique has been used in plant genetic transformation procedures based on tissue culturing (Kaeppler, H. F., Somers, D. A., Rifles, H. W. and Cockburn, A. F. 1992. Silicon carbide fiber—mediated stable transformation of plant cells.

Theor. Appl. Genet. 84:560–566). Such an approach, is restricted by low regeneration potential of cereals in general, and maize in particular, limiting its application to elite cultivars. Moreover, this method provides only about 10% of the efficiency achieved by microparticle bombardment of the embryogenic tissues.

The present invention combines an improved process of pollination pathway and silicon fiber treatment that permits solving the above mentioned problems by delivering the transforming DNA into pollen grains and then, via the sperm, into the egg cells. This novel and non-obvious solution allows to achieve high frequency of maize transformation, and in other crops as well. Beside high efficiency and low cost, its most important advantages are high reproducibility, genotype independence, genetic stability of the transformants, and technical simplicity. These features, taken together, comprise a novel combination which allows said invention to become a basis for large-scale genetic transformation, especially in maize, but in other crops as well. The uniqueness of combining the pollination pathway and the delivering of the transforming DNA into pollen grains by silicon carbide fibers is that the method takes advantages of the natural reproduction system resulting in transformed zygotes.

The advantages of the developed strategy include: (1) expensive and time-consuming tissue culture techniques are not required, (2) genotype-independence, since the method does not require in vitro regeneration procedures, (3) elimination of plant sectoring (mosaicism), since the transformants result from zygotes, (4) no somaclonal variation and reduced fertility caused by prolonged tissue culturing, (5) the use of natural delivery system ensures high stability of the integrated DNA, (6) potential to transfer large fragments of alien DNA into the plant genome; and (7) low cost, high frequency and reproducibility.

Another important advantage of the present method is the possibility of using it for plant transformation (primarily cereals) by large fragments of DNA, e.g. cloned in yeast artificial chromosomes. This allows an increase in the efficiency of map-based cloning of genes of agronomical importance.

2. SUMMARY OF THE INVENTION

A method for plant transformation with resistant properties against antibiotics, herbicides as well as enhanced anthocyanin is provided.

The present invention is directed to a method for genetic transformation of any plant species with sexual reproduction based on a pollination-fecundation process, and its products thereof. According to the present invention the recipient plants are pollinated by pollen grains carrying the transforming DNA wherein the pollen grains are pre-treated by silicon carbide fibers and the transforming DNA. Accordingly, the present invention provides an improved process which combining the pollination pathway and the delivery of the transforming DNA into pollen grains by silicon carbide fibers. The method also allows the possibility to conduct controlled crosses.

The invention, more specifically, provides a method for plant transformation comprising pollination pathway and silicon fiber treatment such that the delivery of transforming DNA into pollen grains. The invention provides a novel and non-obvious process that allows high frequency of maize transformation, and in other crops as well. Beside high efficiency and low cost, its most important advantages and high reproducibility, genotype independence, genetic stability of the transformants, and technical simplicity. The invention further provides a method combining the pollination pathway and the delivering of the transforming DNA into pollen grains by silicon carbide fibers, which takes advantage of the natural reproduction system resulting in transformed zygotes.

The invention provides transgenic plants of the above-described method.

The invention also provides a paste comprising mixing silicon carbide fibers, pollen germination medium and DNA molecules.

Further objects and advantages of the present invention will be clear from the description that follows.

3. BRIEF DESCRIPTION OF FIGURES

Figure 5:

FIG. 5 describes the reaction of a (putative) double transformation on local herbicide application.

4. DETAILED DESCRIPTION OF THE INVENTION

For the description and examples that follow, a number of terms are used herein. In order to provide a clear and consistent understanding of the specification and claims, including the scope to be given such terms, the following definitions are provided.

Definitions: Unless otherwise noted, terms are to be understood according to conventional usage by those of ordinary skill in the relevant art. It addition to the definitions of terms provided below, definitions of common terms in molecular biology may also be found in Lewin, Genes V, Oxford University Press: New York, 1994.

Genotype—The genetic complement of an organism.

Heterologous DNA—DNA from a source different than that of the recipient cell.

Homologous DNA—DNA from the same source as that of the recipient cell.

Hybrid—Progeny resulting from a cross between parental lines.

Inbred Lines—Organisms that are genetically homogeneous (homozygous) resulting from many generations of self crossing.

Monocot—Plants having a single cotyledon (the first leaf of the embryo of seed plants); examples include cereals such as maize, rice, wheat, oats and barley.

Non-Embryogenic Callus—A type of callus composed of undifferentiated, often highly vacuolated cells which are unable to be induced to form embryos.

Phenotype—Traits exhibited by an organism resulting from the interaction of genotype and environment.

Protoplast—Plant cells exclusive of the cell walls.

Somatic Cells—Body cells of an organism, exclusive of germinal cells.

Transformation—Acquisition of new genetic coding sequences by the incorporation of added (exogenous) DNA.

Transgenic—Organisms (plants or animals) into which new DNA sequences are integrated.

Figure 1:
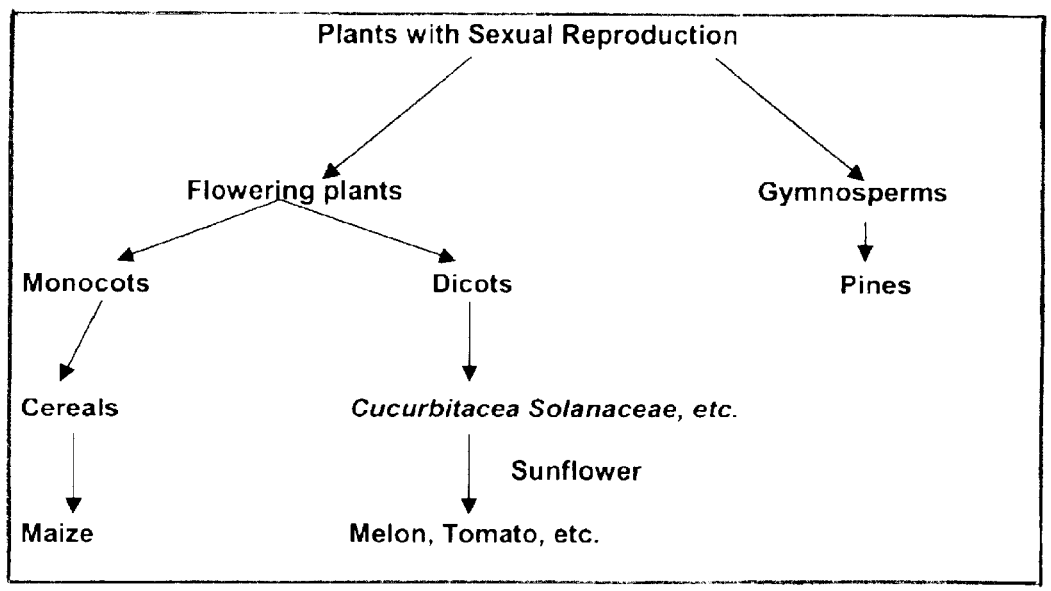
FIG. 1 shows plants with sexual reproduction.

The various fields of application of the present invention include, but are not limited to: (1) monocotyledoneous plants, especially cereal crops (e.g., maize), where conventional transformation methods encounter serious (and frequently non-overcome) difficulties; (2) any flowering plant species with a high number of seeds per fruit (to be more exact, per unit artificial pollination, e.g., melon, tomato). The second group could be any plant species, if even other transformation methods have been used for it but were found technically complex; (3) gemnosperm plants (e.g., pines). In summary, these fields of application could be presented as depicted in FIG. 1.

The present invention addresses one or more of the foregoing or other shortcomings in the prior art by providing methods and products for the genetic transformation of any plant species with sexual reproduction based on a pollination-fecundation process using silicon carbide fibers.

The present invention thus relates generally to methods and products based on a pollination-fecundation process. As used herein, the term transgenic plants is intended to refer to plants that have incorporated exogenous genes or DNA sequences, including but not limited to genes or DNA sequences which are perhaps not normally present, genes not normally transcribed and translated ("expressed") in a given cell type, or any other genes of DNA sequences which one desires to introduce into the non-transformed plant, such as genes which may normally be present in the non-transformed plant but which one desires to have altered expression.

Exemplary genes which may be introduced include, for example, DNA sequences or genes from another species, or even genes or sequences which originate with or are present in the same species, but are incorporated into recipient cells by genetic engineering methods rather than classical reproduction or breeding techniques. However, the term exogenous, is also intended to refer to genes which are not normally present in the cell being transformed, or perhaps simply not present in the form, structure, etc. as found in the transforming DNA segment or gene, or genes which are normally present yet which one desires, e.g., to have over-expressed. Thus, the term "exogenous" gene or DNA is intended to refer to any gene or DNA segment that is introduced into a recipient cell, regardless of whether a similar gene may already be present in such a cell.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance, increased yields, insect and disease resistance, physical appearance, food content and makeup, etc. For example, one may desire to incorporate one or more genes encoding herbicide resistance. A potential insect resistance gene, which can be introduced includes the *Bacillus thuringensis* crystal toxin gene, which may provide resistance to pests such as lepidopteran or coleopteran. Protease inhibitors may also provide resistance. Moreover, the expression of juvenile hormone esterase directed towards specific insect pests may also have insecticidal activity, or perhaps cause cessation of metamorphosis.

Genes encoding proteins characterized as having potential insecticidal activity, such as the cowpea trypsin inhibitor (CpTI) may find use as a rootworm deterrent; genes encoding avermectin may prove particularly useful as a corn rootworm deterrent. Furthermore, genes encoding lectins may, additionally or alternatively, confer insecticide properties (e.g., barley, wheat germ agglutinin, rice lectins), while others may confer antifungal properties (e.g., UDA (stinging nettle lectin), hevein, chitinase).

It is proposed that benefits may be realized in terms of increased resistance to cold temperatures through the introduction of an "antifreeze" protein such as that of the Winder Flounder.

Ultimately, the most desirable "traits" for introduction into a monocot genome may be homologous genes or gene families which encode a desired trait (e.g., increased yield per acre) and which are introduced under the control of novel promoters or enhancers, etch, or perhaps even homologous or tissue specific (e.g., root specific) promoters or control elements.

Because neither genomic or cDNA clones contain transcription and translation signals necessary for expression once transferred and integrated into a plant genome, they must, therefore, be engineered to contain a plant expressible promoter, a translation initiation codon (ATG), and a plant functional poly (A) addition signal (AATAAA) 3' of its translation termination codon. Unique restriction enzyme sites at the 5' and 3' ends of the cassette are typically included to allow for easy insertion into a re-existing construct, such as a plasmid or phage.

Any of a number of transcription initiation regions (i.e., promoters) that direct transcription in plant cells is suitable. The promoter can be either constitutive or inducible. It can be of bacterial origin, viral origin, or eukaryotic origin, such as plant origin. Examples of constitutive plant promoters useful for expressing genes in plant cells include, but are not limited to, the cauliflower mosaic virus (CaMV) 35 S promoter, maize ubiquitin (Ubi-1) promoter, rice actin (Act) promoter, nopaline synthase promoter, and the octopine synthase promoter. A variety of plant gene promoters that are regulated in response to environmental, hormonal, chemical, and/or developmental signals also can be used for expression of foreign genes in plant cells, including promoters regulated by heat (e.g., heat shock promoters); light (e.g., pea rbcS-3A or maize rbcS promoters or chlorophyll a/b-bidning protein promoter); phytohormones, such as abscisic acd; wounding (e.g., wunI); anaerobiosis (e.g., Adh); and chemicals such as methyl jasmonate, salicylic acid, or safeners. Well known cell-, tissue-, organ-, and other developmental stage-specific promoters also can be used.

In addition to a promoter sequence, the expression cassette should also contain a transcription termination region downstream of the gene to provide for efficient termination. The termination region may be obtained from the same gene as the promoter sequence or may be obtained from different genes.

If the mRNA transcribed from the genes is to be efficiently processed, DNA sequences which direct polyadenylation of the RNA are also commonly added to the vector construct. Polyadenylation sequences include, but are not limited to, the Agrobacterium octopine synthase signal, and the nopaline synthase signal. Replication sequences, of bacterial or viral origin, or generally also included to allow the cassette to be cloned in a bacterial or phage host.

Selectable marker genes can be incorporated into the present expression cassettes and used to select for those cells or plants which have become transformed. The marker gene employed may express resistance to an antibiotic, such as kanamycin, gentamycin, 0418, hygromycin, streptomycin, spectinomycin, tetracyline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

The particular marker employed will be one which will allow for the selection of transformed cells as opposed to those cells which are not transformed. Depending on the number of different host species one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4chloro-3indoyl-β-D-glucuronide (X-Gluc).

In developing the present expression construct, i.e., expression cassette, the various components of the expression construct such as the DNA molecules, linkers, or fragments thereof will normally be inserted into a convenient cloning vector, such as a plasmid or phage, which is capable or replication in a bacterial host, such as $E. coli$. Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

The above detailed description should not be construed to unduly limit the present invention as modification and variations in the embodiments discussed herein can be made by those ordinary skill in the art without departing from the spirit or scope of the present invention. The scope of the invention is not to be considered limited thereto.

Conventional methods of gene isolation, molecular cloning, vector construction, silicon carbon fiber techniques, and plant pollination techniques, etc., are well known in the art. One skilled in the art can readily reproduce the plasmids vectors described below without undue experimentation employing these methods in conjunction with the cloning information provided hereto. The various DNA sequences, fragments, etc., necessary for this purpose can be readily obtained as components of commercially available plasmids and their applications in various plant species, or otherwise well known in the art.

The references cited herein evidence the level of skill in the art to which the present invention pertains. The contents of each of these references, including the references cited herein incorporated by reference by their entirety.

The present invention discloses a method for genetic transformation of any plant species with sexual reproduction based on a pollination-fecundation process. In essence, the method comprises the following steps in which;

(a) preparing silicon carbide fibers solution;
(b) preparing pollen germination medium;
(c) mixing the silicon carbide fibers with DNA and with the germination medium;
(d) putting fresh pollen into the above mixture resulting in a paste;
(e) vortexing the mixture for 30–60 seconds;
(f) applying the resulting paste for pollination;
(g) selecting the transformants.

EXAMPLE 1

Genetic Transformation in Maize

Fertile transgenic maize plants were obtained by introducing the bacterial nptII gene encoding kanamycin resistance into zygotes by the pollination-fecundation process. The genomic copy of the gene Sh has been transferred as well and its inheritance was detected in the progeny of stable transformants.

Figure 2:
FIG. 2 depicts the effect of kanamycin on chlorophyll development in maize seedling.

Three different plasmids were used for gene transfer experiments: pCT2T3 and pGV1SOI which carry the NOS promoter expressing the nptll gene as a selectable marker; the third plasmid, pBR322::Sh, contained a cloned genomic copy of Sh Maize stocks used in the experiments were MK159, C22, W64B, Rad391139 and a multi-marker line (wsp31glg12v4; wx sh). DNA was applied to silks of recipient plants as follows: a certain amount of fresh pollen of a recipient plant, taken in time of full flowering, was first immersed in the DNA solution. Then, immediately the paste-like pollen/DNA solution was placed onto the silks of the same recipient plant, thus producing self-pollination. Experimental plants yielded nearly 200 ears with about 25,000 seeds. The first stage of screening for transformants has been done using kanamycin resistance of seedlings. The selected seedlings were green and more vigorous than others, with a more developed root system. Kanamycin sensitive seedlings lost chlorophyll after 10–14 days (FIG. 2, see variant 2 and segregants in variant 3), discontinued their growth and eventually died.

The total DNA from selected resistant genotypes was analyzed using Southern-blot hybridization. The presence of hybridization zones of the nptII gene in the DNA of selected resistant seedlings was demonstrated. The hybridization test with DNA of control plants showed no positive results Pollen from the above transformants was germinated on standard artificial media with kanamycin addition of 200 tg/ml. A ratio of approximately 1:1 of germinated to ungerminated pollen grains has been obtained in this test. Pollen from control plants have not germinated at the kanamycin concentration mentioned. The selfed progeny of fertile transformants was evaluated in vitro using MSmedia with kanamycin. Segregation ratios of green to light-yellow (i.e., resistant to sensitive) close to 3.1 have been obtained Southern-blot analysis showed the presence of DNA sequences homologous to the nptII gene in the genome of green genotypes and its absence in light-yellow ones.

A clone of the normal allele of the sh (shrunken) gene was also used as a selectable marker to overcome the problems associated with the in vitro cultivation and to make the procedure of transformant selection as simple as possible. A multimarker line, ws31glg12v4; wx sh, was used as a recipient in pollination experiments with pBR322::Sh plasmid containing a genomic copy of Sh gene in this case. As a result, ears have been found carrying some smooth seeds (presumed transformants Sh) the remaining seeds being shrunken (sh). No such exceptions have been observed in the control material.

The range of transformation frequency was 0.25–0.53, average 0.35. A series of tests have been conducted for evaluate the effect of transformation on plant fertility. On the average, about 10–20% of the putative transformants have shown different morphological anomalies, including 5–10% of sterile plants. Another important question was the stability of the obtained transformants. All of the selected transformants for kanamycin appeared to segregate in the progeny; about 10 homozygous lines were selected that were tested for stability till T5, and two lines were tested till T8. Besides one case (out of ten), the material showed stable manifestation of resistance. The situation with the Sh marker was quite different. In many cases (more than a third) the selected smooth seeds resulted in a selfed progeny with totally mutant (not transformed) seeds. In other cases (less than 100/-) the selfed progeny gave segregation ratios of the Sh sh closer to 1 3 (or even less) than to the expected ratio 3:1.

Thus, genetic transformation in maize has been demonstrated successfully, using different recipient lines and plasmids with different markers by exploiting pollination fecundation pathway to deliver alien genetic material into the embryo sac.

EXAMPLE 2

Silicon Carbide Fiber-Mediated Genetic Transformation in Maize

Maize transformation via the pollination pathway was initiated in order to improve the pollination-based transformation technique. Several plasmids with different selectable markers were used in pollination experiments of 600 maize plants of three different lines. We used the following genes as selectable markers:

(i) neomycin phosphotransferase (npt II) gene encoding resistance to the antibiotic kanamycin (in the plasmid pBI121 which also contains the GUS reporter gene);

(ii) phosphinothricin acetyltransferase gene (bar) providing resistance to the herbicide bialaphos in the plasmid pBARGUS. The advantage of this construct is that it contains the Adhl gene intron of maize which was shown to increase the expression in maize; and (iii) anthocyanin regulators (C1) from maize controlling anthocyanin production (pAL69).

The study was performed using two maize lines: A619 and T403. We have tested the methods of DNA application using DNA concentrations 50–200 ng/ml). The plasmids containing the different selectable markers used for this pollination experiment were used. Altogether 600 maize plants were pollinated and 5,000 seeds were harvested.

Figure 3:
FIG. 3 depicts the non-transformed (left) and (presumably) transformed for R gene (right) maize plants.
Figure 4:
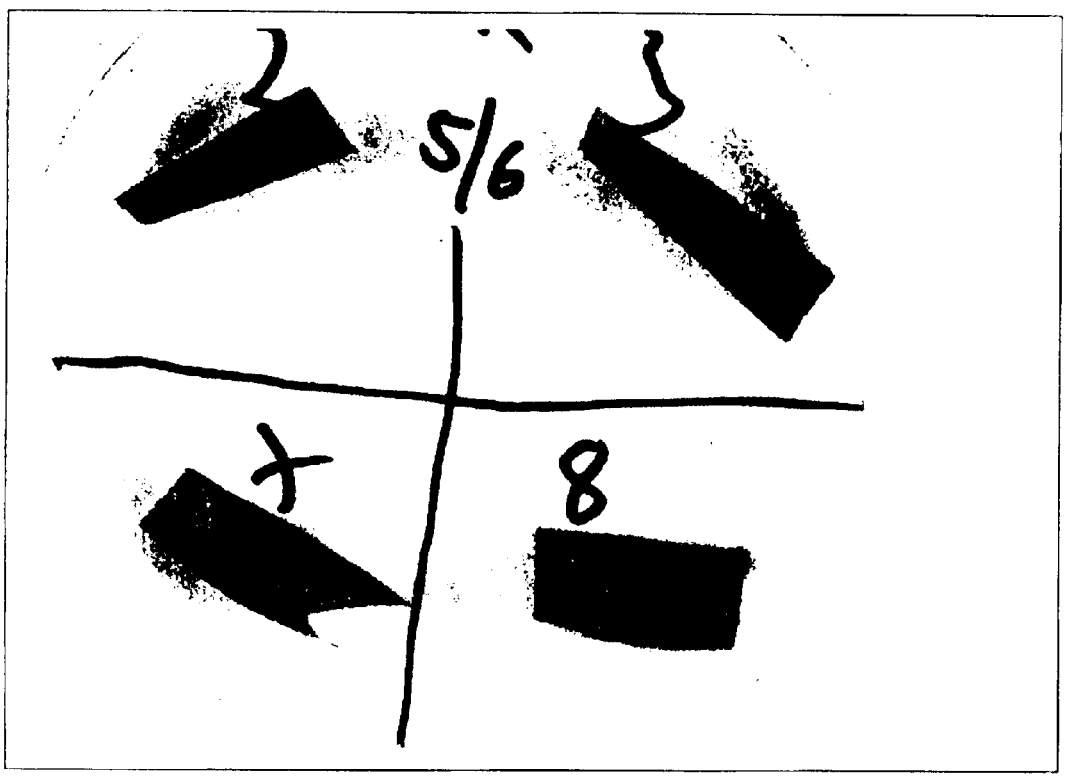
FIG. 4 depicts the effect of kanamycin on chlorophyll development in maize isolated leaves.

These experiments showed promising results which support the proposed strategy of maize transformation. Using silicon-fiber mediated transformation via the pollination pathway, we were able to produce dozens of putative transformants. These plants showed expression of anthocyanin caused by the transforming gene R and/or resistance to the herbicide 'basta' encoded by the Bar gene (FIG. 3) and kanamycin resistance (FIG. 4). An interesting and important result was the demonstration of co-transformation in transposition. Using a mixture of two plasmids carrying the R gene and Bar gene we obtained putative transformants for both. Moreover, it appeared that some putative transformants for Bar manifested a strong increase in expression of R-dependent anthocyanin synthesis after application of the herbicide (FIG. 5). This result corroborates the known involvement of anthocyanin synthesis in stress reactions in plants.

These results indicate that the silicon fiber technique increased the efficiency of transformation several folds: the new treatment has produced 1.7% putative transformant (anthocyanin-expressing) seeds, while the old treatment gave only 0.35%. The results obtained with the old method (no fiber treatment) are rather similar to those obtained in Kishinev.

Preparation of silicon carbide fibers: 50 mg. of fibers (0.1–20 $\mu$m average diameter and 10–1.0–250 $\mu$m length, e.g., produced by Advanced Composite Materials Corps, 1525 S. Buncombe Rd., Greer, S.C. 29651) are autoclaved in 1.5 ml tubes. Then, 5% solution is prepared by adding 1 ml sterile water.

Preparation of pollen germination medium: The solution contains 15% sucrose, 0.018% $H_3BO_3$, 0–04% Ca ($NO_3$) $2-4H_2O$, pH 5.6 This solution is autoclaved for 20 minutes.

Mixing fibers with DNA and germination medium: Plasmid DNA in TE solution (25–100 $\mu$g dissolved) is mixed with 40 $\mu$l of fiber solution (5%), vortexed for a few seconds and incubated for 5 minutes at room temperature. Then, 500 $\mu$l of pollen germination medium is added.

Pollen treatment: Fresh pollen (200 mg) is put into 500 $\mu$l of the above mixture and vortexes for 30–60 seconds.

Application of the treated pollen: The resulting paste is applied immediately for pollination, 250 $\mu$l for the silks of each ear. The ears are then covered by paper bags.

Selection of the transformants: The selection is performed on the basis of specific cloned selectable markers which have either phenotypic expression (e.g., anthocyanin) or provide resistance to some drugs (e.g. antibiotics or herbicides).

Our results obtained for several putative transformants selected for anthocyanin expression provide further confirmation for the presence of the foreign transforming DNA encoding for herbicide resistance (Basta) in the genome of these T1 plants and its transmission to the next generation (T2 plants) (Table 1).

TABLE 1

Results of Progeny Testing Of Some Putative Transformants Obtained In Co-Transformation Experiments

| # of genotypes | Phenotype of Anthocyanin PG | T1 Basta RS | Segregation at Anthocyanin (PG) | T2 Basta (RS) |
| --- | --- | --- | --- | --- |
| 424 | P | R | 13:5 | 4:7 |
| 116 | P | S | 13:5 | 0:2 |
| 98 | P | R | 10:5 | 5:1 |
| 111 | P | S | 9:10 | 2:2 |
| 121 | P |  | 8:11 | 3:0 |
| 45 | P | S | 7:11 | 0:4 |
| 392 | C |  | 0:12 | 4:14 |
| 49 | P light | S | 7:11 | 1:1 |
| Control | C | S | 0:9 | 0:7 |

Notes: P and G - pink and green color, R and S - resistant and susceptible

What is claimed is:

1. A method for genetic transformation of tomato or melon, said method comprising the steps of:

(a) preparing a silicon carbide fibers solution;

(b) preparing a pollen germination medium;

(c) preparing a DNA solution;

(d) mixing said silicon carbide fiber solution with said pollen germination medium and said DNA solution to form a mixture;

(e) adding fresh pollen into said mixture to form a paste;

(f) vortexing said paste for 30–60 seconds, thereby producing a vortexed paste;

(g) applying said vortexed paste on female reproduction plant parts of melon or tomato plants for pollination; and (h) selecting transformants.

2. The method of claim 1, wherein the silicon carbide fibers of said silicon carbide fiber solution are approximately 0.1–20 μm diameter and 1–250 μm length.

3. The method of claim 2, wherein said silicon carbide fibers are between 1–2 μm in diameter and 10–180 μm in length.

4. The method of claim 1, wherein the silicon carbide fiber solution comprises a sufficient amount of sterile water or solvent, to make a 5% to 25% aqueous solution.

5. The method of claim 1, wherein said pollen germination medium is a solution containing about 5%–15% sucrose, 0.01%–1.0% $H_3BO_3$, 0.01% to 1.0% $Ca(NO_3)_2 4H_2O$ at pH 5.6.

6. The method of claim 5, wherein the pollen germination medium contains about 15% sucrose, 0.018% $H_3BO_3$, 0.04% $Ca(NO_3)_2 4H_2O$ at pH 5.6.

7. The method of claim 1, wherein said DNA solution is a solution of plasmid DNA.

8. The method of claim 7, wherein said plasmid DNA is dissolved in a Tris EDTA solution.

9. The method of claim 1, wherein selection of transformants is based on the phenotypic expression of a selectable marker gene, wherein the gene confers antibiotic resistance or herbicide resistance on the transformants or affects anthocyanin coloration of the transformants.

10. The method of claim 9, wherein said selectable marker gene with a phenotypic expression is a gene regulating anthocyanin levels.

11. The method of claim 9, wherein said selectable marker gene is a gene providing resistance to at least one antibiotic.

12. The method of claim 9, wherein said selectable marker gene encodes neomycin phosphotransferase.

13. The method of claim 9, wherein said selectable marker gene is a gene providing resistance to kanamycin.

14. The method of claim 9, wherein said selectable marker gene encodes phosphinothricin acetyltransferase.

15. A method for genetic transformation of sexually reproducing maize, said method comprising the steps of:

(a) preparing a silicon carbide fiber solution;

(b) preparing a pollen germination medium;

(c) preparing a DNA solution;

(d) mixing said silicon carbide fiber solution with said pollen germination medium and said DNA solution to form a mixture;

(e) adding fresh pollen into said mixture to form a paste;

(f) vortexing said paste for 30 to 60 seconds, thereby producing a vortexed paste;

(g) applying said vortexed paste on silks of maize plants for pollination; and (h) selecting transformants.

16. The method of claim 15, wherein the silicon carbide fibers of said silicon carbide fiber solution are approximately 0.1–20 μm in diameter and 1–250 μin length.

17. The method of claim 16, wherein said silicon carbide fibers are between 1–2 μm in diameter and 10–180 μm in length.

18. The method of claim 15, wherein the silicon carbide fiber solution comprises a sufficient amount of sterile water or solvent, to make a 5% to 25% aqueous solution.

19. The method of claim 15, wherein the pollen germination medium contains about 5%–15% sucrose, 0.01%–1.0% $H_3BO_3$, 0.01% to 1.0% $Ca(NO_3)_2 4H_2O$ at pH.

20. The method of claim 19, wherein the pollen germination medium contains about 15% sucrose, 0.018% $H_3BO_3$, 0.04% $Ca(NO_3)_2 4H_2O$ at pH 5.6.

21. The method of claim 15, wherein said DNA solution is a solution of plasmid DNA.

22. The method of claim 21, wherein said solution of plasmid DNA is dissolved in a Tris EDTA solution.

23. The method of claim 15, wherein selection of transformants is based on the phenotypic expression of a selectable marker gene, wherein the gene confers antibiotic resistance or herbicide resistance on the transformants or affects anthocyanin coloration of the transformants.

24. The method of claim 23, wherein said selectable marker gene is a gene providing resistance to neomycin phosphotransferase.

25. The method of claim 23, wherein said selectable marker gene is a gene providing resistance to kanamycin.

26. The method of claim 23, wherein said selectable marker gene encodes phosphinothricin acetyltransferase.

* * * * *